(12) United States Patent
Mick et al.

(10) Patent No.: US 6,911,000 B2
(45) Date of Patent: Jun. 28, 2005

(54) DISPOSABLE AND SHIELDED SEED MAGAZINE AND SPACER MAGAZINE ASSEMBLY

(75) Inventors: Felix Mick, Bronxville, NY (US); Kenneth Zabrouski, Bethpage, NY (US)

(73) Assignee: Mick Radio-Nuclear Instruments, Inc., Mount Vernon, NY (US)

( * ) Notice: Subject to any disclaimer, the term of this patent is extended or adjusted under 35 U.S.C. 154(b) by 67 days.

(21) Appl. No.: 10/351,034

(22) Filed: Jan. 24, 2003

(65) Prior Publication Data

US 2003/0144571 A1 Jul. 31, 2003

Related U.S. Application Data

(60) Provisional application No. 60/351,601, filed on Jan. 25, 2002.

(51) Int. Cl.⁷ .............................. A61N 5/00; A61M 3/00
(52) U.S. Cl. ........................................................... 600/7
(58) Field of Search ........................................... 600/1–8

(56) References Cited

U.S. PATENT DOCUMENTS

| | | | | |
|---|---|---|---|---|
| 5,242,373 A | * | 9/1993 | Scott et al. | 600/7 |
| 5,860,909 A | * | 1/1999 | Mick et al. | 600/7 |
| 6,007,474 A | * | 12/1999 | Rydell | 600/7 |
| 6,013,020 A | * | 1/2000 | Meloul et al. | 600/7 |
| 6,213,932 B1 | * | 4/2001 | Schmidt | 600/7 |
| 6,306,074 B1 | * | 10/2001 | Waksman et al. | 600/7 |
| 6,358,195 B1 | * | 3/2002 | Green et al. | 600/7 |
| 2002/0120174 A1 | * | 8/2002 | Steele et al. | 600/7 |

* cited by examiner

*Primary Examiner*—Samuel G. Gilbert
(74) *Attorney, Agent, or Firm*—Kenyon & Kenyon

(57) ABSTRACT

A magazine assembly for use in a medical instrument, for example, a radioactive seed applicator, includes a housing, a cartridge, a seed plunger and a spring element. The housing is formed of a material adapted to shield transmission of radioactive energy.

13 Claims, 6 Drawing Sheets

DISPOSABLE AND SHIELDED SEED MAGAZINE AND SPACER MAGAZINE ASSEMBLY

CROSS-REFERENCE TO RELATED APPLICATIONS

The present application claims the benefit of U.S. Provisional Application Ser. No. 60/351,601, filed on Jan. 25, 2002, which is expressly incorporated herein in its entirety by reference thereto.

FIELD OF THE INVENTION

The present invention relates to a disposable and shielded seed magazine for use in a medical instrument. The present invention also relates to a spacer magazine assembly for use in a medical instrument.

BACKGROUND INFORMATION

Medical instruments, particularly, seed applicators, are used to implant radioactive seeds into a patient's body. Such seed applicators are described, for example, in U.S. Pat. No. 5,860,909, which is expressly incorporated herein in its entirety by reference thereto.

Since the seeds are radioactive, it is an object of the present invention to provide a disposable cartridge or magazine for a seed applicator that is shielded to limit transmission of radioactive energy.

The seed applicator described in U.S. Pat. No. 5,860,909 is designed to implant seeds at spaced locations in a patient's body. The spacing of the seeds by the seed applicator is provided by selection and engagement of indentations on a barrel of the applicator with a ball plunger. It is also possible to provide the desired spacing between subsequent seeds by delivering and implanting absorbable spacers between seeds. It is an object of the present invention to provide a spacer magazine assembly configured and adapted for use in conjunction with such spacer and seed arrangement.

SUMMARY

The above and other beneficial objects of the present invention are achieved by providing a disposable and shielded seed cartridge or magazine as described herein and by providing a spacer magazine assembly as described herein.

According to one example embodiment of the present invention, the seed magazine includes a housing formed of a material adapted to limit transmission of radioactive energy from the radioactive seeds contained therein. Such shielding may be beneficial for shipping purposes, for preparation purposes and for equipment and personnel safety purposes.

According to an example embodiment of the present invention, the seed magazine includes a cartridge portion configured to receive at least one radioactive seed and a housing portion formed of a material having a radiation shield effectiveness substantially equal to that of lead for at least one of I-125, TI-201, Xe-133, Tc-99m and Pd-103. The cartridge portion may be configured to receive a plurality of seeds. The material of the housing portion may include a thermoplastic material and may be lead-free. The material may be injection moldable and may include approximately 94% filler material by weight. The material may have at least one of a density of approximately 6.90 gms/cc, a flexural yield of approximately 11,946 psi, a flexural modulus of approximately 1,210,000 psi, a tensile modulus of approximately 1,542,000 psi, an ultimate tensile strength of approximately 6,946 psi, an ultimate elongation of approximately 0.795%, a notched izod impact strength of approximately 1.202 ft-lb/in, a linear mold shrinkage of approximately 0.005 to 0.006 in/in and a material density of approximately 62.5% compared to lead. The material may be autoclaveable.

The material may include a brass material and/or a brass alloy, e.g., C36000.

The seed magazine may include a seed plunger configured to eject the seed from the cartridge portion, and the seed magazine may be configured to be non-refillable after ejection of the at least one seed.

The housing may be configured to connect to a seed applicator device.

DETAILED DESCRIPTION

Figure 2:
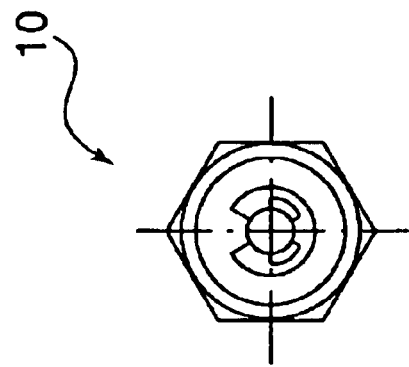
FIG. 2 is a side elevational view of the magazine assembly illustrated in FIG. 1.
Figure 1:
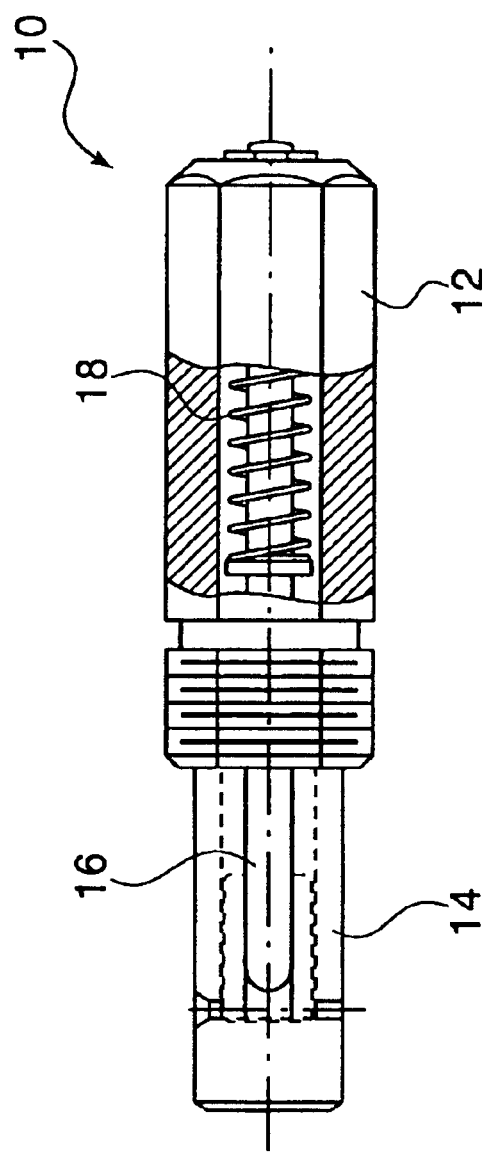
FIG. 1 is a top plan view, partially in cross-section, of an example embodiment of a disposable and shielded seed magazine assembly according to the present invention.

FIG. 1 is a top plan view, partially in cross-section, of an example embodiment of a disposable and shielded seed magazine assembly 10 according to the present invention, and FIG. 2 is a side elevational view of the magazine assembly 10 illustrated in FIG. 1. As illustrated in FIG. 1, the magazine assembly 10 includes a housing 12, a cartridge 14, a seed plunger 16 and a spring element 18. The magazine assembly 10 may be configured for use in conjunction with a medical instrument or seed applicator device, such as that described in U.S. Pat. No. 5,860,909, which is expressly incorporated herein in its entirety by reference thereto. The magazine assembly 10 is adapted to receive, for example, fifteen seeds. The magazine assembly 10 may be disposable after use.

As illustrated in FIGS. 1 and 2, the housing 12 has a hexagonal cross-section. It should be appreciated, however, that the housing 12 may have any desired cross-sectional configuration, including, for example, a circular cross-section.

The housing 12 may be formed of an autoclaveable, nontoxic, high-density thermoplastic composite material.

The material may be lead-free, may be injection moldable, may provide a greater yield strength compared to lead and may include approximately 94% filler material by weight. An example material for the housing 12 may have a density, per ASTM Test Method D-792, of approximately 6.90 gms/cc, a flexural yield, per ASTM Test Method D-790, of approximately 11,946 psi, a flexural modulus, per ASTM Test Method D-790, of approximately 1,210,000 psi, a tensile modulus, per ASTM Test Method D-638, of approximately 1,542,000 psi, an ultimate tensile strength, per ASTM Testing Method D-638, of approximately 6,946 psi, an ultimate elongation, per ASTM Testing Method D-638, of approximately 0.795%, a notched izod impact strength, per ASTM Testing Method D-256, of approximately 1.202 ft-lb/in and a linear mold shrinkage, per ASTM Testing Method D-955, of approximately 0.005 to 0.006 in/in, or any combination thereof. An example material for the housing 12 may have a material density of approximately 62.5% compared to lead. Furthermore, an example material for the housing 12 may providing approximately 100% shield effectiveness relative to lead for I-125 (major radiation energy at 35.5 keV gamma), TI-201 (major radiation energy at 71 keV gamma), Xe-133 (major radiation energy at 81 keV gamma) and Tc-99m (major radiation energy at 152 keV gamma), Pd-103, or any combination thereof. It should be understood that the magazine assembly 10 may be shielded or partially shielded. The housing 12 may alternatively be formed of a brass material, e.g., C36000 alloy.

Figure 3:
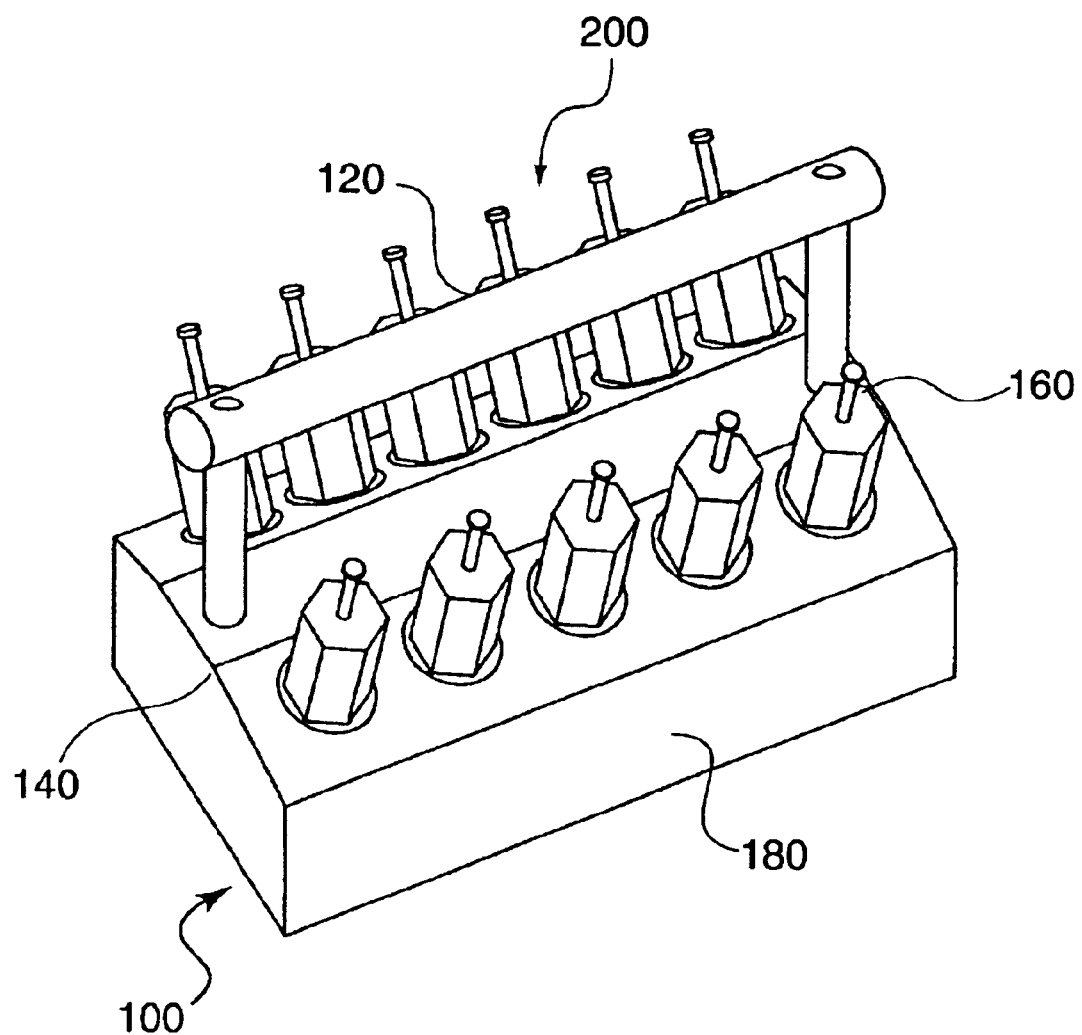
FIG. 3 is a perspective view of a plurality of magazine assemblies arranged in a sterilizing block.

FIG. 3 is a perspective view of a plurality of magazine assemblies according to the present invention arranged in a sterilizing block 100. Measurements of several example embodiments of a magazine assembly according to the present invention at various locations 120, 140, 160, 180 around the sterilizing block 100. The measurements were taken at 10 cm from the surface of the sterilizing block 100 with each magazine assembly threaded into to the sterilizing block. The measurements were taken with an Eberline detector HP-270, model E120.

A first example embodiment of a magazine assembly according to the present invention, which is configured as a partially shielded disposable cartridge. The housing 12 of the first example embodiment was formed of the thermoplastic material described above. The first example embodiment included a total of 150 seeds (fifteen seeds per cartridge, ten cartridges total) with isotope I-125, having an activity/seed of 0.729 mCi and a total activity of 109.350 mCi. A background reading of approximately 0.02 mR/h was obtained. At the handle location 120, a reading of 23 mR/h was obtained; at the location 140, a reading of 0.03 mR/h was obtained; at the location 160, a reading of 0.03 mR/h was obtained; and at the location 180, a reading of 0.60 mR/h was obtained.

A second example embodiment of a magazine assembly according to the present invention, which is configured as a reusable cartridge formed of stainless steel. The second example embodiment included a total of 100 seeds (ten seeds per cartridge, ten cartridges total) with isotope I-125, having an activity/seed of 0.729 mCi and a total activity of 72.9 mCi. A background reading of approximately 0.02 mR/h was obtained. At the handle location 120, a reading of 0.02 mR/h was obtained; at the location 140, a reading of 0.02 mR/h was obtained; at the location 160, a reading of 0.02 mR/h was obtained; and at the location 180, a reading of 0.02 mR/h was obtained.

A third example embodiment of a magazine assembly according to the present invention, which is configured as a shielded disposable cartridge. The housing 12 of the third example embodiment was formed of the thermoplastic material described above. The third example embodiment included a total of 150 seeds (fifteen seeds per cartridge, ten cartridges total) with isotope I-125, having an activity/seed of 0.729 mCi and a total activity of 109.350 mCi. A background reading of approximately 0.02 mR/h was obtained. At the handle location 120, a reading of 0.04 mR/h was obtained; at the location 140, a reading of 0.02 mR/h was obtained; at the location 160, a reading of 0.02 mR/h was obtained; and at the location 180, a reading of 0.50 mR/h was obtained.

A fourth example embodiment of a magazine assembly according to the present invention, which is configured as a shielded disposable cartridge. The housing 12 of the fourth example embodiment was formed of the brass material described above. The fourth example embodiment included a total of 150 seeds (fifteen seeds per cartridge, ten cartridges total) with isotope I-125, having an activity/seed of 0.354 mCi and a total activity of 53.1 mCi. A background reading was set to zero mR/h. At the handle location 120, a reading of 0.02 mR/h was obtained; at the location 140, a reading of 0.02 mR/h was obtained; at the location 160, a reading of 0.02 mR/h was obtained; and at the location 180, a reading of 0.04 mR/h was obtained. At a top location 200, a reading of 0.04 mR/h was obtained.

Figure 4:
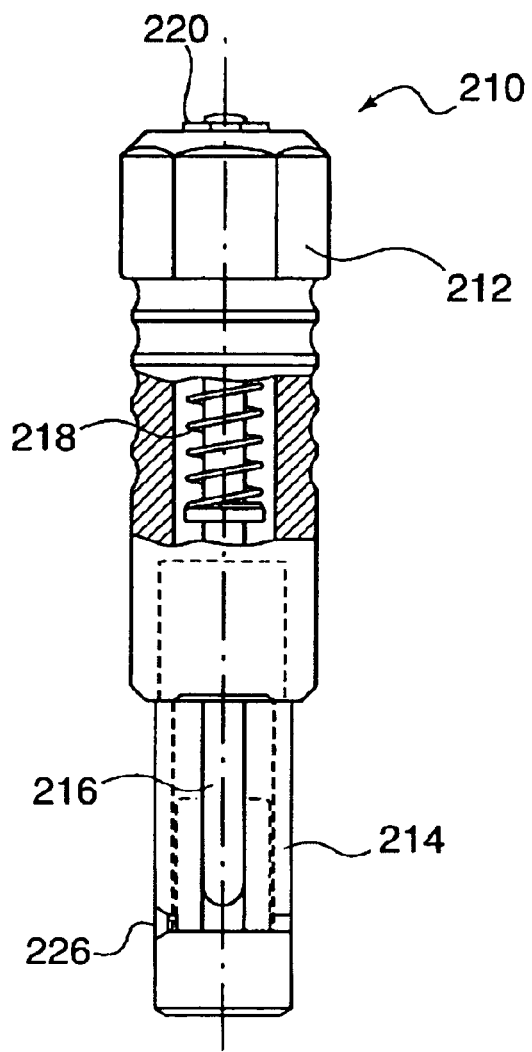
FIG. 4 is a front view of a spacer magazine assembly according to the present invention.
Figure 5:
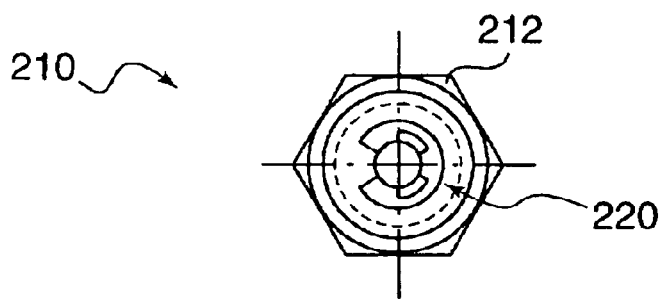
FIG. 5 is an end view of the spacer magazine assembly illustrated in FIG. 4.

FIG. 4 is a front view of an example embodiment of a spacer magazine assembly 210 according to the present invention. The spacer magazine assembly 210 includes a head portion 212, a cartridge portion 214, a plunger portion 216 and a spring member 218. The spring member 218 is arranged to bias the plunger portion 216 in the downward direction as illustrated in FIG. 4. As illustrated in FIG. 5, which is an end view of the spacer magazine assembly 210, an E-ring 220 maintains the plunger portion 216 in engagement with the head portion 212 and cartridge portion 214. It should be understood that the cartridge portion 214 is adapted by size and configuration to receive a number, e.g., a predetermined number and combination, e.g., alternatingly, of seeds and/or spacers, which are biased by the plunger portion 216 in the downward direction as illustrated in FIG. 4 toward the distal end of the cartridge portion 214. As further described below, the cartridge portion 214 includes a bore 226 for delivery of the seeds and/or spacers therethrough to be delivered to the treatment site. The spacers may be formed of an absorbable material, e.g., an absorbable polymer.

Figure 6:
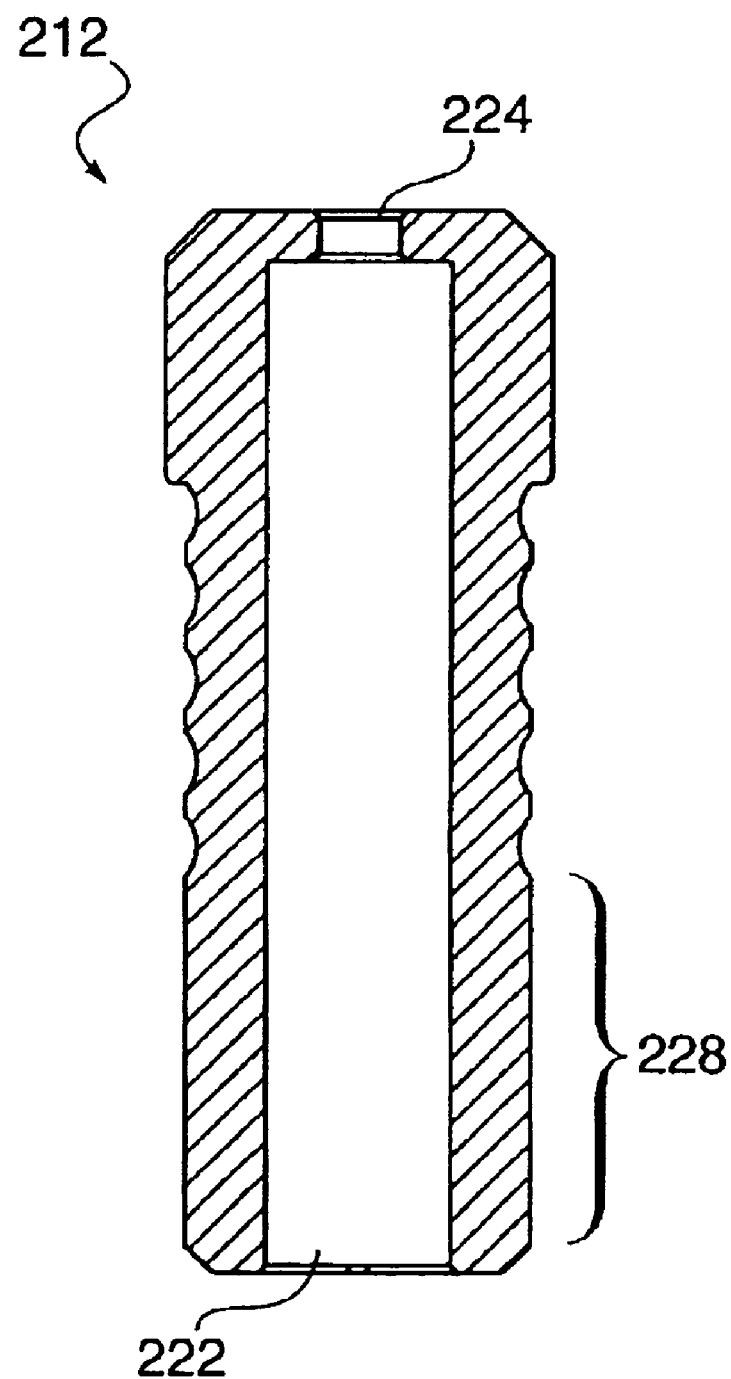
FIG. 6 is a front cross-sectional view of a head portion of the spacer magazine assembly illustrated in FIGS. 4 and 5.

FIG. 6 is a front cross-sectional view of the head portion 212 of the spacer magazine assembly 210. As illustrated in FIG. 6, the head portion includes a bore 222 arranged to receive the plunger portion 216 and a bore 224 through which an end of the plunger portion 216 extends. The head portion 212 may include a threaded, e.g., internally-threaded, end 228 engageable with a complementary threaded, e.g., externally-threaded, end of the cartridge portion 214. It should be understood that the cartridge portion 214 and the head portion 212 may be engageable in accordance with any mechanism and arrangement and that the treaded ends described herein are merely exemplary.

Figures 7, 8:
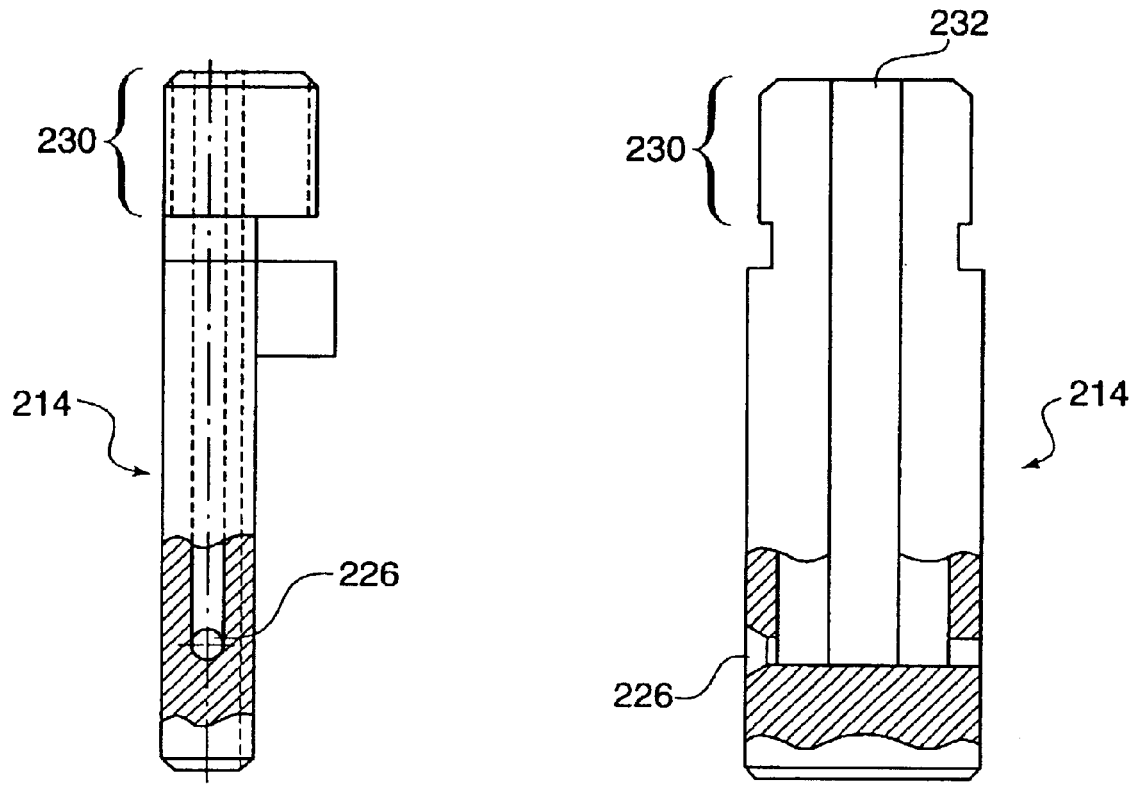
FIG. 7 is a front view of a cartridge portion of the spacer magazine assembly illustrated in FIGS. 4 and 5.
FIG. 8 is a side view of the cartridge portion illustrated in FIG. 7.
Figure 9:
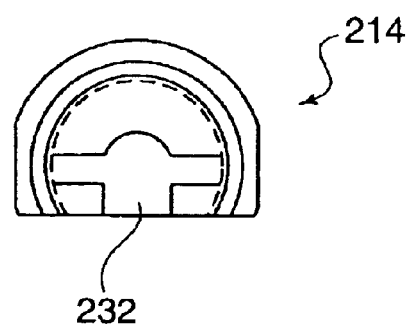
FIG. 9 is an end view of the cartridge portion illustrated in FIGS. 7 and 8.

FIG. 7 is a front view of the cartridge portion 214 of the spacer magazine assembly 210, FIG. 8 is a side view of the cartridge portion 214, and FIG. 9 is an end view of the cartridge portion 214. The cartridge portion 214 includes a threaded, e.g., externally-threaded, end 230 engageable with the threaded, e.g., internally-threaded, end 228 of the head portion 212. The cartridge portion 214 also includes a bore 232 arranged to receive the plunger portion 216 and a magazine of seeds and/or spacers. The arrangement of the bore 232 is complementary to the arrangement of the plunger portion 216, which is more fully described below and includes a circular bore portion and a slotted portion. A bore 226 is arranged in the cartridge portion 214 and is adapted to deliver the seeds and/or spacers therethrough for delivery to the treatment site. One or both ends of the bore 226 may be countersunk to facilitate delivery of the seeds and/or spacers and to prevent interference and/or binding with the delivery needle.

Figure 11:
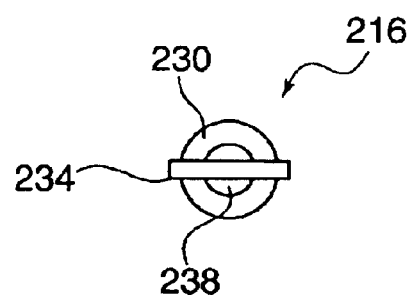
FIG. 11 is an end view of the plunger portion illustrated in FIG. 10.
Figure 10:
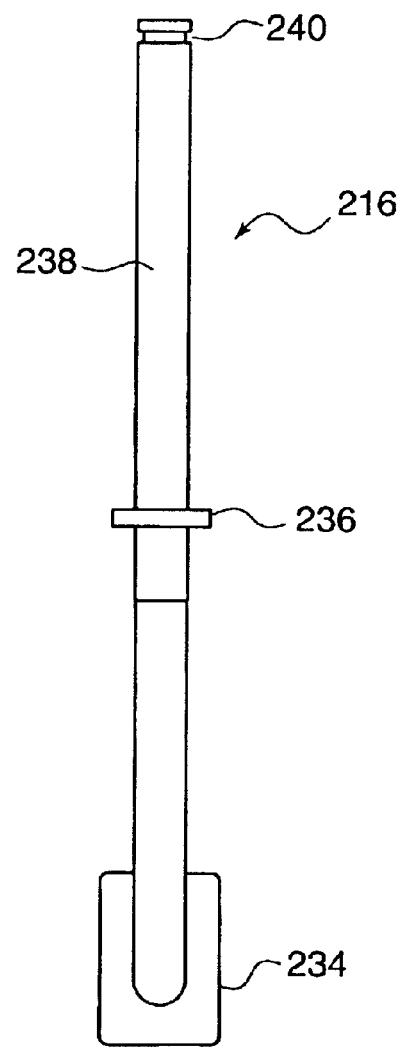
FIG. 10 is a front view of a plunger portion of the spacer magazine assembly illustrated in FIGS. 4 and 5.

FIG. 10 is a front view of the plunger portion 216, and FIG. 11 is an end view of the plunger portion 216. The plunger portion 216 includes a shaft 238, a shoulder adapted to abut one end of the spring member 218, an enlarged end portion 234 and a groove 240 adapted to receive the E-ring 220. The enlarged end portion 234 is arranged to bore 232 of the cartridge portion 214, and the end having the groove 240 is adapted to be inserted through the bore 224 of the head portion 212. The enlarged end portion 234 is adapted by size and configuration to urge the seeds and/or spacers arranged in the cartridge portion 214 by the bias of the spring member 218 toward the bore 226 in the cartridge portion. As each seed and/or spacer is ejected from the cartridge portion 214, the plunger advances a subsequent seed and/or spacer toward the bore 226 to be subsequently ejected and delivered to the treatment site.

What is claimed is:

1. A seed magazine, comprising:
    a cartridge portion configured to receive at least one radioactive seed; and
    a housing portion formed of a material having a radiation shield effectiveness substantially equal to that of lead for at least one of I-125, Tl-201, Xe-133, Tc-99 m and Pd-103,
    wherein the material includes approximately 94 % filler material by weight.

2. The seed magazine according to claim 1, wherein the cartridge portion is configured to receive a plurality of seeds.

3. The seed magazine according to claim 1, wherein the material includes a thermoplastic material.

4. The seed magazine according to claim 1, wherein the material is lead-free.

5. The seed magazine according to claim 1, further comprising a seed plunger configured to eject the seed from the cartridge portion.

6. The seed magazine according to claim 1, wherein the cartridge portion is configured to be non-refillable after ejection of the at least one seed.

7. The seed magazine according to claim 1, wherein the material is injection moldable.

8. The seed magazine according to claim 1, wherein the housing portion is configured to connect to a seed applicator device.

9. The seed magazine according to claim 1, wherein the material is autoclaveable.

10. A seed magazine, comprising:
    a cartridge portion configured to receive at least one radioactive seed; and
    a housing portion formed of a material having a radiation shield effectiveness substantially equal to that of lead for at least one of I-125, Tl-201, Xe-133, Tc-99 m and Pd-103,
    wherein the material has at least one of a density of approximately 6.90 gms/cc, a flexural yield of approximately 11,946 psi, a flexural modulus of approximately 1,210,000 psi, a tensile modulus of approximately 1,542,000 psi, an ultimate tensile strength of approximately 6,946 psi, an ultimate epongation of approximately 0.795 %, a notched izod impact strength of approximately 1.202 ft-lb/in, a linear mold shrinkage of approximately 0.005 to 0.006 in/in and a material density of approximately 62.5 % compared to lead.

11. A seed magazine, comprising:
    a cartridge portion configured to receive at least one radioactive seed; and
    a housing portion formed of a material having a radiation shield effectiveness substantially equal to that of lead for at least one of I-125, Tl-201, Xe-133, Tc-99 m and Pd-103,
    wherein the material includes a brass material.

12. A seed magazine, comprising:
    a cartridge portion configured to receive at least one radioactive seed; and
    a housing portion formed of a material having a radiation shield effectiveness substantially equal to that of lead for at least one of I-125, Tl-201, Xe-133, Tc-99 m and Pd-103,
    wherein the material includes a brass alloy.

13. A seed magazine, comprising:
    a cartridge portion configured to receive at least one radioactive seed; and
    a housing portion formed of a material having a radiation shield effectiveness substantially equal to that of lead for at least one of I-125, Tl-201, Xe-133, Tc-99 m and Pd-103,
    wherein the brass alloy includes C36000.

* * * * *